United States Patent [19]

Foley

[11] Patent Number: 5,042,467
[45] Date of Patent: Aug. 27, 1991

[54] MEDICATION INHALER WITH FITTING HAVING A SONIC SIGNALLING DEVICE

[75] Inventor: Martin P. Foley, London, Canada

[73] Assignee: Trudell Medical, London, Canada

[21] Appl. No.: 577,292

[22] Filed: Sep. 4, 1990

Related U.S. Application Data

[63] Continuation of Ser. No. 501,359, Mar. 28, 1990, abandoned, which is a continuation of Ser. No. 293,083, Jan. 3, 1989, abandoned.

[51] Int. Cl.$^5$ .............. A61M 11/00; A62B 7/00; A62B 9/00
[52] U.S. Cl. .............. 128/200.23; 128/200.14; 128/205.23
[58] Field of Search ............ 128/200.23, 203.12, 128/203.29, 200.14, 205.23

[56] References Cited

U.S. PATENT DOCUMENTS

| 4,291,688 | 9/1981 | Kistler | 128/200.23 |
| 4,470,412 | 9/1984 | Nowacki et al. | 128/200.23 |
| 4,484,577 | 11/1984 | Sackner et al. | 128/200.23 |
| 4,790,305 | 12/1988 | Zoltan et al. | 128/203.28 |
| 4,809,692 | 3/1989 | Nowacki et al. | 128/203.29 |

Primary Examiner—Edgar S. Burr
Assistant Examiner—Kimberly L. Asher
Attorney, Agent, or Firm—Robert M. Wolters

[57] ABSTRACT

A medication inhaler includes an elongated hollow body for improved misting of the medication. A sonic signalling device is provided which is exposed to the inside of the inhaler and to outside air. The sonic signalling device comprises an integrally molded plastic body and vibratory reed. If a person inhales too rapidly, the reed will be set in vibration by reduced pressure inside the inhaler, whereby to generate a pleasant musical tone to alert the user that he is inhaling too rapidly.

5 Claims, 2 Drawing Sheets

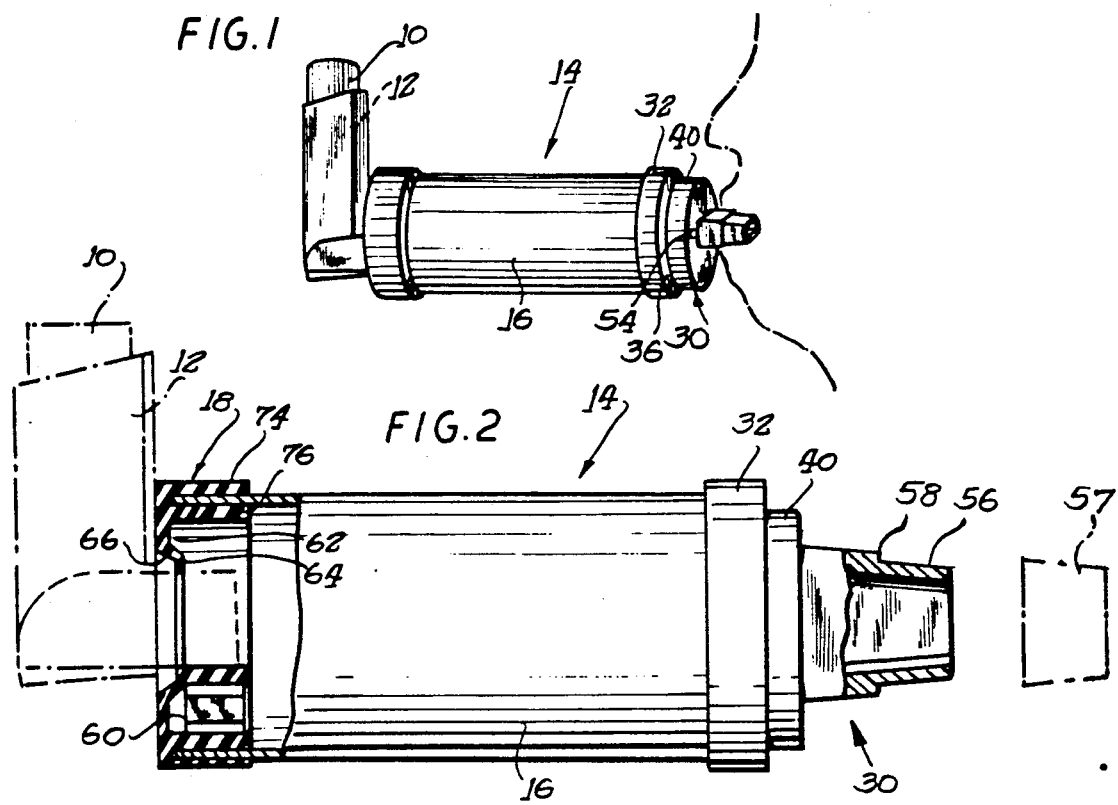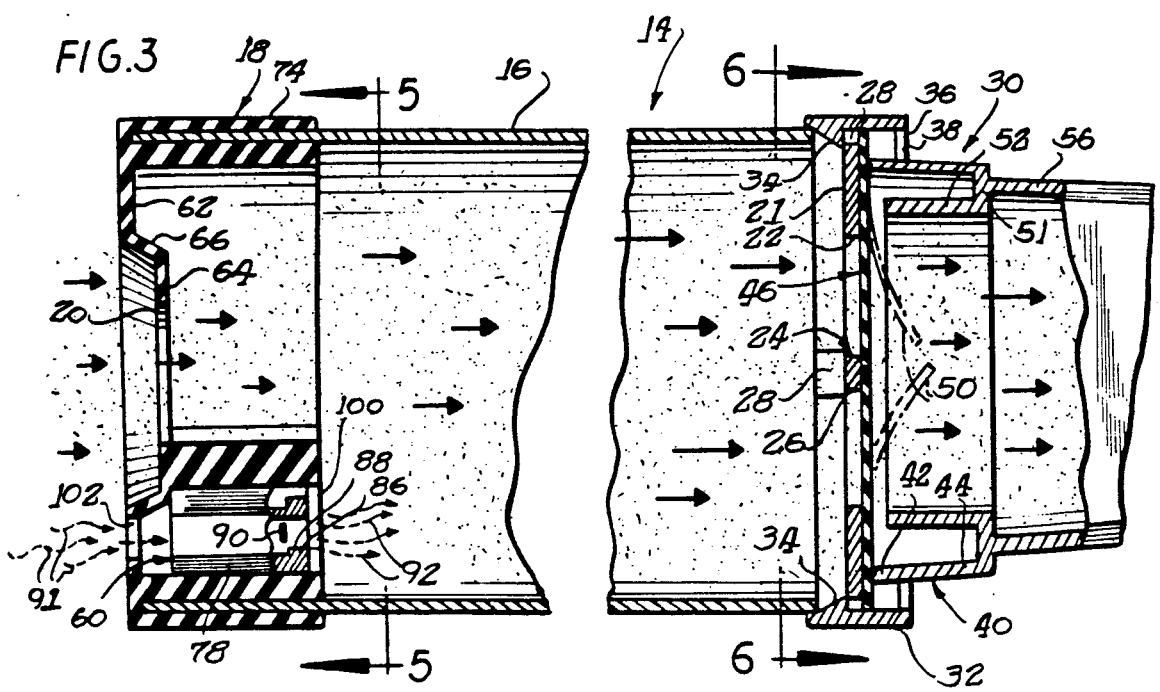

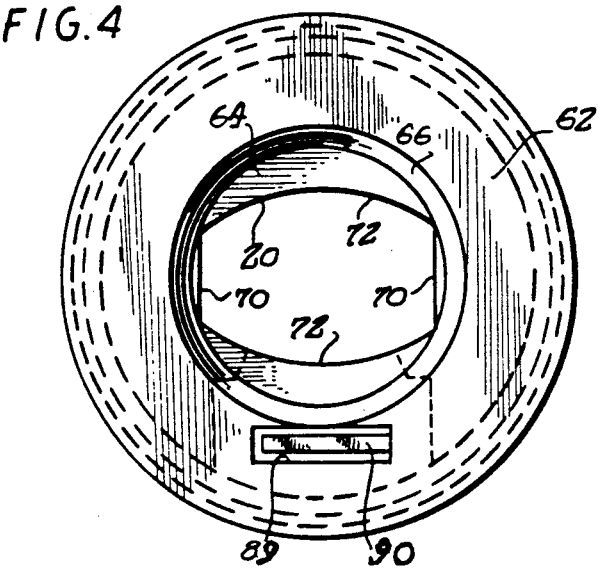
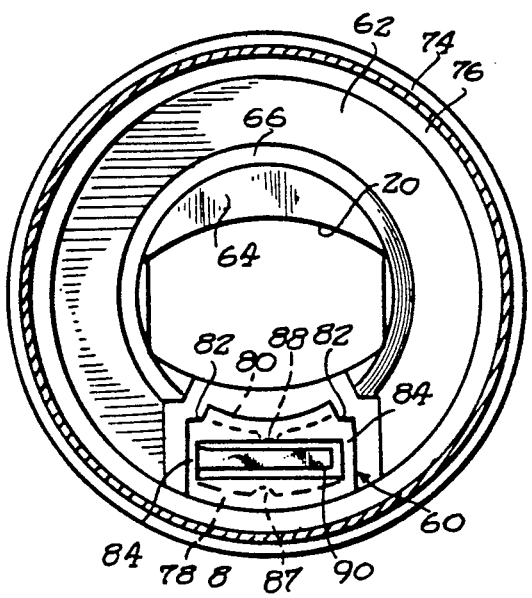
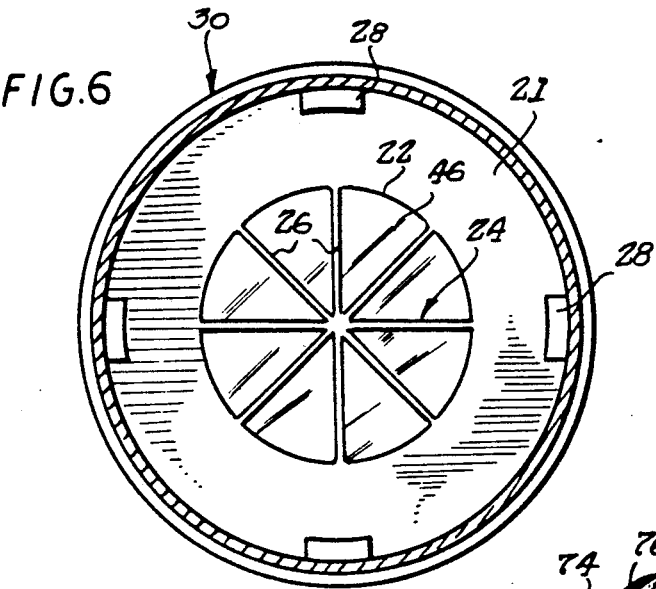
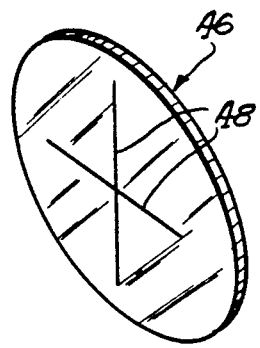
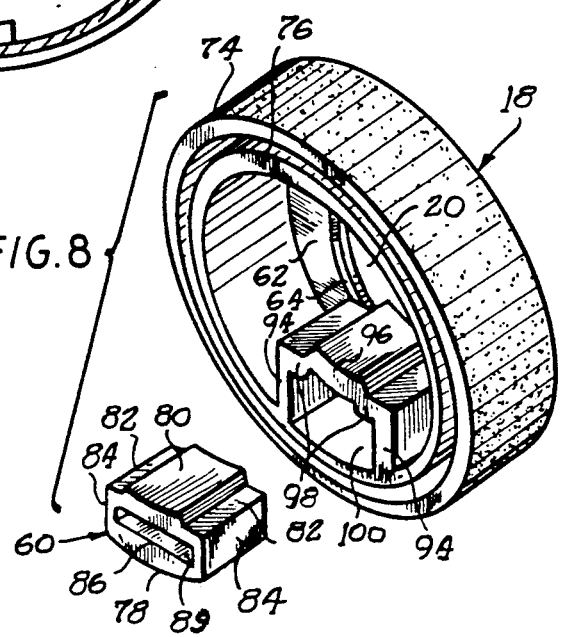

MEDICATION INHALER WITH FITTING HAVING A SONIC SIGNALLING DEVICE

RELATED PATENT APPLICATIONS

This application is a continuation of application Ser. No. 07/501,359, filed Mar. 28, 1990, now abandoned, which was a continuation of application Ser. No. 07/293,083, filed Jan. 3, 1989, now abandoned.

The present invention is related to that disclosed and claimed in Nowacki and Brisson in U.S. Pat. No. 4,470,412 and forms an improvement thereon.

BACKGROUND OF THE INVENTION

A person suffering from asthma and experiencing an asthmatic attack may have rather considerable difficulty in breathing, due to swelling in the bronchi and due to secretion of mucus. There are various antiasthmatic pills that are effective but which generally are somewhat slow-acting. There are also medications available for intravenous treatment which work quite rapidly, but which require administration by skilled medical personnel. For most asthmatic sufferers, the promptest, immediately available relief is by way of an inhalant. Epinephrine or other suitable asthmatic medication is packaged with a suitable diluent in a small pressurized canister or cartridge which interfits with a mouthpiece. The patient places the mouthpiece in his mouth, and depresses the cartridge, thereby releasing a measured amount of medication which is inhaled through the mouthpiece.

Some patients do not inhale properly, and the mouthpiece may not be completely effective in cooperation with the cartridge to convert the medication into a mist which is deposited in the proper bronchial area to relieve the asthmatic attack. Often there are small droplets of medication, rather than a mist, and this may be compounded by improper inhalation which results in much of the medication simply going into the throat and stomach where it is ineffective against the asthmatic attack.

In accordance with U.S. Pat. No. 4,470,412 mentioned above, a cylindrical chamber is provided which has at one end a plastic or an elastomeric adapter which receives the mouthpiece of the cartridge device. The opposite end of the cylindrical chamber is provided with a mouthpiece or equivalent, and a one-way valve in the chamber adjacent the downstream or mouthpiece end precludes back-flow upon exhalation by the person suffering the asthmatic attack. Passage of the medication through the chamber completes formation of the medication released into the desired mist.

Some sufferers tend to inhale too strongly. This can cause leakage of air into the chamber, and resulting dilution of the medication. This is undesirable. It also possible that medication would be drawn through the bronchi too rapidly, thus not having an opportunity to deposit and take effect in the proper areas. Inhalation should be at a controlled rate so that substantially all of the medication will be effective in the alveolus, and not carried into the bronchi tree where it does not do any good. Although inhalation by a person suffering from an asthmatic attack may be difficult panic may nevertheless be such as to cause inhalation that is too rapid.

OBJECTS AND SUMMARY OF THE INVENTION

In accordance with the present invention, an asthmatic or the like medication inhaler is provided having a warning device to alert asthmatic sufferer if he inhales too vigorously.

Thus, the principal object of the present invention is to provide an asthmatic medication inhaler which signals a warning to the asthmatic sufferer if he inhales to too vigorously.

It is a further object of the present invention to provide such a medication inhaler having an auditory warning, specifically an auditory warning which has a pleasant tone, but which is readily discernible to the asthmatic sufferer.

In carrying out the foregoing and other objects and advantages of the present invention, an air operated auditory warning device is incorporated in the plastic or elastomeric adapter at the entering end of the chamber. The auditory warning device comprises a plastic molding having an air passageway partially closed at the downstream end by an integral tongue or reed. Any upstream movement of air through the device would have no effect on the reed. However, if the asthmatic sufferer inhales too vigorously, then a sufficient lowering of pressure in the medication inhaler chamber will occur to cause drawing of air through the auditory device, thereby causing the reed to vibrate, and generating a musical tone, very similar to the air induced vibration of a harmonica reed.

THE DRAWINGS

The invention will best be understood with reference to the following text when taken in connection with the accompanying drawings wherein:

FIG. 1 is a perspective view of a medication inhaler with warning as constructed in accordance with the present invention, showing the use thereof;

FIG. 2 is a side view, partially in section, of the inhaler;

FIG. 3 is an enlarged, fragmentary side view of the medication inhaler of the present invention, partially in section, showing the movement of air and medication therethrough;

FIG. 4 is an end view taken from the left end of FIG. 3;

FIG. 5 is a cross-sectional view taken substantially along the line 5—5 in FIG. 3;

FIG. 6 is a cross-sectional view taken substantially along the line 6—6 in FIG. 3;

FIG. 7 is a perspective view showing the diaphragm or valve of the medication inhaler; and FIG. 8 is a perspective view showing the auditory warning device in juxtaposition to the rubber or elastomeric adapter in which it is inserted.

DETAILED DISCLOSURE OF THE ILLUSTRATIVE EMBODIMENT

Reference should first be made to FIG. 1 and 2 wherein there will be seen a prior art pressurized canister or cartridge 10, sometimes referred to as a nebulizer and is charged with epinephrine or other suitable antiasthmatic medication and a suitable diluent, and under pressure. The cartridge fits into the receiving end of a right angle mouthpiece 12, the opposite end of which is designed to be placed in the asthmatic sufferer's mount. The cartridge is pressed down, being squeezed between the index finger and the thumb underlying the mouthpiece. This causes a valve stem in the cartridge to press against a reaction base in the mouthpiece to discharge a measured quantity of medication into the mouthpiece. The discharge is supposed to be in the form of a mist, but in fact often contains small droplets. The patient inhales, and the mist passes into the mouth, and hopefully into the bronchial tubes to provide asthmatic relief. The patient is then supposed to hold his breath for a short time, and subsequently to exhale slowly through nearly closed lips. However, as heretofore noted, some of the medication may simply be in the form of droplets, not mist, and the droplets generally do not reach the bronchial tubes to effect their intended purpose.

In accordance with U.S. Pat. No. 4,470,412, mentioned above, the drops can be broken up in a mist, and the patient cam be more or less forced to inhale properly with the use of the medication inhaler shown in such patient and detailed hereinafter.

The medication inhaler is shown generally in FIGS. 2 and 3, and attention should now be directed to these two figures. The medication inhaler is indicated generally by the number 14 and includes a cylindrical body 16 molded of semi-rigid plastic resin. The chamber is open at both ends. A resinous plastic or elastomeric adapter or fitting 18 is received on the entering or upstream end of the chamber and includes a central opening 20 adapted resiliently to grip the horizontal portion of the mouthpiece 12 which is intended to be placed in a person's mouth. Further details of the adapter or receiver 18 will be sent forth in greater detail hereinafter.

At the opposite end of the cylindrical chamber 16 there is a right angle inwardly extending flange 21 integral with the side wall of the cylinder and defining a central circular aperture 22 having a spider 24 (FIG. 6) thereacross and comprising equally arcuately spaced legs 26. The flange 20 and adjacent sidewall of the cylindrical chamber 16 are provided with four equally arcuately spaced recesses or notches 28. An end cap 30 is provided at the downstream end (the right end in FIGS. 1-3) and is molded of the same plastic resin material as the cylindrical chamber. The end cap 30 includes at the left end thereof a cylindrical flange of proper diameter to embrace the open end of the cylindrical cartridge 14. The flange 32 is provided with inwardly directed cam teeth 34 for snapping into the notches 28 to secure the end cap 30 on the cylindrical chamber 16. A radial flange 36 extends inwardly from the right edge of the cylinder 32 and is molded integrally therewith. Apertures 38 are formed in this flange to provide enhanced flexibility in the area of the teeth 34, and also to provide for clearance for various portions of the mold. A generally cylindrical, but slightly tapered wall 40 is formed integrally with the flange 36, and extends to the left thereof at 42, and also through the right thereof at 44.

A flat plastic or elastomeric diaphragm 46 (see also FIGS. 6 and 7) having a circular periphery fits within the cylinder 32 of the end cap 30 and is held against the flange 20 by the leftwise projection 42 of the wall 40. This leaves the center portion of the diaphragm entirely free, except that it is backed by the spider 24. The diaphragm is provided with a pair of right angle, intersecting slits 48 that are backed by two of the spider legs 26. When one uses the inhaler as will be described in greater detail later, the diaphragm deflects to the right as shown in broken lines at 50 in FIG. 3, to open the slits, and to allow air and medication to pass freely past the diaphragm. However, if one attempts to exhale through the inhaler, the diaphragm presses tightly against the spider 24 and air cannot pass to the left of the diaphragm.

A flange 50 extends inwardly from the right end of the tapered cylindrical wall 40 and has integral therewith a cylindrical flange 52 extending to the left. This wall terminates short of the diaphragm 46. A pair of diametrically spaced apertures 54 (FIG. 1) are provided in the wall 51 so that if one attempts to exhale through the inhaler, the exhaled air passes around the left end of the cylindrical wall 52 and back and out through the openings 54.

The end cap 30 is completed by a tapered extension 56 which is adapted to be received in a person's mouth, and which therefore is wider than it is high.

Both the side walls and the top and bottom walls are arched, being convex outwardly. The entire end cap is a single, one-piece molding. A cover cap 57 may be provided for sanitary purposes to cover the portion of the extension 56 that fits in a person's mouth, and to this end the wall is notched at 58 for best positioning of the cover cap.

Attention now should be directed to FIGS. 2-5 and 8 wherein the adapter or receiver 18 will be seen in greater detail, along with the sonic signalling device 60 forming the subject matter of the present invention. The adapter 18 comprises a front wall 62 adapted to abut the inlet end of the chamber 16. The front wall 62 is provided with a central thinner portion 64 which is offset at 66 inwardly (in a downstream direction) and is provided with the central aperture 20 which is slightly smaller than the portion of the mouthpiece 12 designed to be received in the mouth. This shape includes vertical side walls 70 and outwardly arcuate top and bottom walls 72. The adapter 18 further includes a peripheral flange which extends axially of the chamber 16 and embraces the outer end thereof. This flange is circular, and an inner-circular flange 76 engages the inner wall of the inlet end of the chamber 16.

The sonic or audible signalling device 60 comprises a one-piece molding of polycarbonate plastic resin material. The signaling device is shown as mounted in the lower part of the adapter 18, but it could be in the upper part. It is described as positioned in the lower part for reference purposes. The signalling device comprises a bottom wall 78 which is cylindrical in shape and conforms to the inner wall of the flange 76. An outer wall 80 is also of cylindrical shape, but of slightly less radius than the bottom wall 72 of the aperture 20. The inner or upper wall 80 is narrower than the wall 78, and lateral flat wall extension 82 extend outwardly to vertical side walls 84. Longitudinal ribs 87 and 88 are respectively formed on the outer and inner walls 78 and 80 centrally thereof for reinforcement, and to direct airflow.

The signalling device is approximately 7/16 inch long, and at the exit and (the right end in FIG. 3, and the end viewed in FIG. 8) there is a vertical wall 86 which is substantially 3/32 inch thick, and which is provided with a rectangular orifice 89. At the inner face of the wall 86, there is provided an integral reed 89 which is joined at one end to one of the side walls 84, and which is spaced at the opposite end and along the sides from the margins of the orifice 90. The reed is approximately ½ inch long, and slightly less than 1/16 inch wide. If air passes from the inlet end of the sonic device 60 and through to the outlet end as indicated by the arrows 90 and 92, respectively, the reed will vibrate. When the read vibrates it generates a musical tone similar to that generated by a harmonica, approximately at a note of C one octave above middle C. This provides a pleasant tone which is not annoying to those who might overheat it, yet one which is of somewhat higher pitch than most ambient sounds, thereby being readily heard. If air is forced through the sonic device in the opposite direction, no sound is generated.

The inner face of the flange 76 and extending rearwardly from the wall 64 are provided with side walls 94, and inner arcuate wall 96, and lateral extension walls 98 which form a cavity 100 which snugly receives the sonic device 60. The wall 62 is provided with a rectangular aperture 102 leading into the inlet end of the sonic device 60.

When the 21 of the outlet fitting 30 is placed in the patient's mouth, the patient inhales, and medication is drawn from the mouthpiece 12 upon depression of the cylinder or canister 10 which emits a measured amount of medication. This medication is thoroughly misted within the chamber 16 before entering the patient's mouth, and ultimately his bronchi and lungs. An adult patient should inhale the mist at a rate of less than 30 liters per minute. If he inhales at greater than 30 liters per minute, the medication is not fully effective, as much of it is drawn past bronchi and into the lungs where it has no effect on the asthmatic attack. If a patient does inhale at greater than 30 liters per minute, then the pressure differential between the inside of the device 14 and the outside becomes sufficiently great that air is drawn through the sonic device 60 to cause the reed 90 to vibrate and generate a sound which is readily discerned by the patient or by an overseeing medical person. This alerts the patient and any overseeing medical person to have the patient slow down his inhalation.

The reed does not generate sound with reverse flow, as previously noted, but no reverse flow is to be expected, since if the patient exhales through the device 14 the diaphragm 46 will be pressed against the arms of the spider 24 to close the slits 48 thereof, the exhaled air then being diverted past the forward end of the wall 52 and exiting through the openings 38 and 54.

The specific example of the invention as herein shown and described is for illustrative purposes. Various changes in structure may occur to those skilled in the art, and will be understood as forming a part of the present invention insofar as they fall within the sphere and scope of the appended claims.

The invention is claimed as follows:

1. In a medication inhaler including a cylindrical body having a longitudinal axis of rotation, said body being elongated longitudinally of said axis and defining a passageway having an open entering upstream end and an open exit downstream end, said body being of predetermined length, means at said exit end for coupling to a patient's mouth, one-way valve means in said body across said passageway and permitting flow through said passageway from said entering end to said exit end and preventing flow in the opposite direction, the improvement comprising means at said entering end for receiving structure for applying inhalation medication and for mounting a sonic signalling device, said receiving and mounting means including a flexible fitting disposed transversely across said entering end and secured to said body adjacent said entering end and having a central opening for resiliently receiving and supporting said medication applying structure, said fitting further having an off-center passageway for snugly receiving and supporting a sonic signalling device, and being much shorter than said predetermined length, said medication applying structure being of varying size and shape, and a sonic signalling device, said sonic signalling device being mounted in said off-center passageway in said flexible fitting adjacent said body entering end with said sonic signalling device exposed on opposite sides to ambient air outside of said body and readily hearable outside of said inhaler and to the inside of said body, said sonic signalling device including a body having a passageway having an upstream end opening to ambient air and a downstream exit end opening to the inside of said elongated cylindrical body, and a reed disposed across said sonic signaling means passageway and adapted to vibrate and provide an audible tone if the pressure inside said elongated cylindrical body differs from ambient air pressure by more than a predetermined amount caused by too rapid inhalation by a patient using said inhaler.

2. A medication inhaler as set forth in claim 1 wherein said flexible fitting has a passageway elongated longitudinally in the direction of air flow and resiliently receiving said signalling device body.

3. A medication inhaler as set forth in claim 1 wherein said signalling device passageway has predetermined transverse dimensions throughout most of its length and is provided with a restriction adjacent said downstream end, said reed being disposed transversely across said restriction.

4. A medication inhaler as set forth in claim 3 wherein said signalling device body and said reed comprises an integral plastic molding.

5. A medication inhaler as set forth in claim 1 wherein said signalling device body and said reed comprises an integral plastic molding.

* * * * *